(12) United States Patent
Burger et al.

(10) Patent No.: US 7,507,412 B2
(45) Date of Patent: Mar. 24, 2009

(54) GLYCOPROTEIN VI FUSION PROTEINS

(75) Inventors: Christa Burger, Darmstadt (DE);
Johannes Gleitz, Darmstadt (DE);
Mathias Frech, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/483,810

(22) PCT Filed: Jul. 12, 2002

(86) PCT No.: PCT/EP02/07796

§ 371 (c)(1),
(2), (4) Date: Jan. 15, 2004

(87) PCT Pub. No.: WO03/008454

PCT Pub. Date: Jan. 30, 2003

(65) Prior Publication Data

US 2004/0157300 A1 Aug. 12, 2004

(30) Foreign Application Priority Data

Jul. 18, 2001 (EP) .................................. 01116717

(51) Int. Cl.
*A61K 39/00* (2006.01)
(52) U.S. Cl. .................. 424/192.1; 424/185.1; 530/384; 530/387.3; 530/412
(58) Field of Classification Search ................. 530/350, 530/387.1; 424/192.1, 134.1
See application file for complete search history.

(56) References Cited

U.S. PATENT DOCUMENTS 5,525,491 A * 6/1996 Huston et al. .............. 435/69.7

6,245,527 B1 * 6/2001 Busfield et al. ............ 435/69.1

FOREIGN PATENT DOCUMENTS

| WO | WO 0056885 A1 * | 9/2000 |
| WO | WO00 68377 | 11/2000 |
| WO | WO01 00810 | 1/2001 |
| WO | WO 0118203 A1 * | 3/2001 |

OTHER PUBLICATIONS

Vogel, WF "Collagen-receptor signaling in health and disease" (2001) European Journal of Dermatology, 11:506-514.*
Smethurst et al., "Identification of the primary collagen-binding surface on human glycoprotein VI by site-directed mutagenesis and by blocking pahge antibody" (2004) Blood, 103:903-911.*
D. J. Capon, et al, "Designing CD4 Immunoadhesins for Aids Therapy", *Nature, MacMillan Journals Ltd.*, vol. 337, pp. 525-531 (Feb. 9, 1989).

* cited by examiner

*Primary Examiner*—Michael Szperka
(74) *Attorney, Agent, or Firm*—Millen, White, Zelano & Branigan, P.C.

(57) ABSTRACT

The present invention relates to Glycoprotein VI (GPVI) fusion proteins (GPVI-fusion proteins) comprising a tag like myc, GST, HA, FLAG, STREP but preferably a Immunoglobulin molecule (Ig), more preferably a Fc portion of said Ig and a protein or oligopeptide having the biological activity of GPVI (GPVI-like protein) which is binding to collagen and their use in methods and kits for the screening of potential agonists or antagonists for GPVI-colagen and/or platelet-collagen interaction is disclosed. Further, pharmaaceutical compositions and therapeutic methods are provided comprising such GPVI-fusion proteins for the treatment of thrombotic and cardiovascular events and disorders related to GPVI-collagen and/or platelet-collagen interactions.

17 Claims, 6 Drawing Sheets

Vector map of SK9 coding for Fc-GPVI

Vector map of KL74 coding for GPVI-Fc

SEQUENCE LISTING

<160> NUMBER OF SEQ ID NOS: 12

<210> SEQ ID NO 1
<211> LENGTH: 501
<212> TYPE: PRT
<213> ORGANISM: Artificial
<220> FEATURE:
<223> OTHER INFORMATION: Fc-GPVI fusion protein as encodes in SK9

<400> SEQUENCE: 1

Met Lys Leu Pro Val Arg Leu Leu Val Leu Met Phe Trp Ile Pro Gly
1               5                   10                  15

Glu Glu Arg Gly Lys Glu Pro Lys Ser Ser Asp Lys Thr His Thr Cys
                20                  25                  30

Pro Pro Cys Pro Ala Pro Glu Leu Gly Gly Pro Ser Val Phe Leu
            35                  40                  45

Phe Pro Pro Lys Pro Lys Asp Thr Leu Met Ile Ser Arg Thr Pro Glu
    50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Ala Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175

```
Gly Phe Tyr Pro Ser Asp Ile Ala Val Glu Trp Glu Ser Asn Gly Gln
                180                 185                 190

Pro Glu Asn Asn Tyr Lys Thr Thr Pro Val Leu Asp Ser Asp Gly
            195                 200                 205

Ser Phe Phe Leu Tyr Ser Lys Leu Thr Val Asp Lys Ser Arg Trp Gln
        210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Gln Ser Gly Pro
            245                 250                 255

Leu Pro Lys Pro Ser Leu Gln Ala Leu Pro Ser Ser Leu Val Pro Leu
        260                 265                 270

Glu Lys Pro Val Thr Leu Arg Cys Gln Gly Pro Pro Gly Val Asp Leu
        275                 280                 285

Tyr Arg Leu Glu Lys Leu Ser Ser Ser Arg Tyr Gln Asp Gln Ala Val
        290                 295                 300

Leu Phe Ile Pro Ala Met Lys Arg Ser Leu Ala Gly Arg Tyr Arg Cys
305                 310                 315                 320

Ser Tyr Gln Asn Gly Ser Leu Trp Ser Leu Pro Ser Asp Gln Leu Glu
                325                 330                 335

Leu Val Ala Thr Gly Val Phe Ala Lys Pro Ser Leu Ser Ala Gln Pro
            340                 345                 350

Gly Pro Ala Val Ser Ser Gly Gly Asp Val Thr Leu Gln Cys Gln Thr
        355                 360                 365

Arg Tyr Gly Phe Asp Gln Phe Ala Leu Tyr Lys Glu Gly Asp Pro Ala
        370                 375                 380

Pro Tyr Lys Asn Pro Glu Arg Trp Tyr Arg Ala Ser Phe Pro Ile Ile
385                 390                 395                 400

Thr Val Thr Ala Ala His Ser Gly Thr Tyr Arg Cys Tyr Ser Phe Ser
                405                 410                 415

Ser Arg Asp Pro Tyr Leu Trp Ser Ala Pro Ser Asp Pro Leu Glu Leu
            420                 425                 430

Val Val Thr Gly Thr Ser Val Thr Pro Ser Arg Leu Pro Thr Glu Pro
        435                 440                 445

Pro Ser Ser Val Ala Glu Phe Ser Glu Ala Thr Ala Glu Leu Thr Val
        450                 455                 460

Ser Phe Thr Asn Lys Val Phe Thr Thr Glu Thr Ser Arg Ser Ile Thr
465                 470                 475                 480

Thr Ser Pro Lys Glu Ser Asp Ser Pro Ala Gly Pro Ala Arg Gln Tyr
                485                 490                 495

Tyr Thr Lys Gly Asn
            500

<210> SEQ ID NO 2
<211> LENGTH: 512
<212> TYPE: PRT
<213> ORGANISM: Artificial
<220> FEATURE:
<223> OTHER INFORMATION: GPVI-Fc fusion as encoded in KL74A

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Leu Ala Phe Lys Leu Lys Leu
            20                  25                  30
```

-continued

```
Gln Ser Gly Pro Leu Pro Lys Pro Ser Leu Gln Ala Leu Pro Ser Ser
        35                  40                  45

Leu Val Pro Leu Glu Lys Pro Val Thr Leu Arg Cys Gln Gly Pro Pro
        50                  55                  60

Gly Val Asp Leu Tyr Arg Leu Glu Lys Leu Ser Ser Ser Arg Tyr Gln
65                      70                  75                  80

Asp Gln Ala Val Leu Phe Ile Pro Ala Met Lys Arg Ser Leu Ala Gly
                85                  90                  95

Arg Tyr Arg Cys Ser Tyr Gln Asn Gly Ser Leu Trp Ser Leu Pro Ser
                100                 105                 110

Asp Gln Leu Glu Leu Val Ala Thr Gly Val Phe Ala Lys Pro Ser Leu
            115                 120                 125

Ser Ala Gln Pro Gly Pro Ala Val Ser Ser Gly Gly Asp Val Thr Leu
130                 135                 140

Gln Cys Gln Thr Arg Tyr Gly Phe Asp Gln Phe Ala Leu Tyr Lys Glu
145                 150                 155                 160

Gly Asp Pro Ala Pro Tyr Lys Asn Pro Glu Arg Trp Tyr Arg Ala Ser
                165                 170                 175

Phe Pro Ile Ile Thr Val Thr Ala Ala His Ser Gly Thr Tyr Arg Cys
                180                 185                 190

Tyr Ser Phe Ser Ser Arg Asp Pro Tyr Leu Trp Ser Ala Pro Ser Asp
            195                 200                 205

Pro Leu Glu Leu Val Val Thr Gly Thr Ser Val Thr Pro Ser Arg Leu
            210                 215                 220

Pro Thr Glu Pro Pro Ser Ser Val Ala Glu Phe Ser Glu Ala Thr Ala
225                 230                 235                 240

Glu Leu Thr Val Ser Phe Thr Asn Lys Val Phe Thr Thr Glu Thr Ser
                245                 250                 255

Arg Ser Ile Thr Thr Ser Pro Lys Glu Ser Asp Ser Pro Ala Gly Pro
                260                 265                 270

Ala Arg Gln Tyr Tyr Thr Lys Gly Asn Cys Gly Arg Glu Pro Lys Ser
            275                 280                 285

Ser Asp Lys Thr His Thr Ser Pro Pro Ser Pro Ala Pro Glu Leu Leu
            290                 295                 300

Gly Gly Ser Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
                340                 345                 350

Val His Asn Ala Lys Thr Lys Pro Arg Glu Glu Gln Tyr Asn Ser Thr
            355                 360                 365

Tyr Arg Val Val Ser Val Leu Thr Val Leu His Gln Asp Trp Leu Asn
            370                 375                 380

Gly Lys Glu Tyr Lys Cys Lys Val Ser Asn Lys Ala Leu Pro Ala Pro
385                 390                 395                 400

Ile Glu Lys Thr Ile Ser Lys Ala Lys Gly Gln Pro Arg Glu Pro Gln
                405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
            435                 440                 445

Glu Trp Glu Ser Asn Gly Gln Pro Glu Asn Asn Tyr Lys Thr Thr Pro
```

```
            450                 455                 460
Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
                500                 505                 510
```

```
<210> SEQ ID NO 3
<211> LENGTH: 4
<212> TYPE: PRT
<213> ORGANISM: Artificial
<220> FEATURE:
<223> OTHER INFORMATION: Peptide linker

<400> SEQUENCE: 3

Ala Ala Ala Ala
1

<210> SEQ ID NO 4
<211> LENGTH: 5
<212> TYPE: PRT
<213> ORGANISM: Artificial
<220> FEATURE:
<223> OTHER INFORMATION: Peptide linker

<400> SEQUENCE: 4

Ala Ala Ala Ala Ala
1               5

<210> SEQ ID NO 5
<211> LENGTH: 4
<212> TYPE: PRT
<213> ORGANISM: Artificial
<220> FEATURE:
<223> OTHER INFORMATION: Peptide linker

<400> SEQUENCE: 5

Gly Gly Gly Gly
1

<210> SEQ ID NO 6
<211> LENGTH: 5
<212> TYPE: PRT
<213> ORGANISM: Artificial
<220> FEATURE:
<223> OTHER INFORMATION: Peptide linker

<400> SEQUENCE: 6

Gly Gly Gly Gly Gly
1               5

<210> SEQ ID NO 7
<211> LENGTH: 7
<212> TYPE: PRT
<213> ORGANISM: Artificial
<220> FEATURE:
<223> OTHER INFORMATION: Peptide linker

<400> SEQUENCE: 7

Gly Gly Gly Gly Gly Gly Gly
1               5

<210> SEQ ID NO 8
<211> LENGTH: 5
```

```
<212> TYPE: PRT
<213> ORGANISM: Artificial
<220> FEATURE:
<223> OTHER INFORMATION: Peptide linker

<400> SEQUENCE: 8

Gly Gly Pro Gly Gly
1               5

<210> SEQ ID NO 9
<211> LENGTH: 5
<212> TYPE: PRT
<213> ORGANISM: Artificial
<220> FEATURE:
<223> OTHER INFORMATION: Peptide linker

<400> SEQUENCE: 9

Gly Gly Gly Gly Ser
1               5

<210> SEQ ID NO 10
<211> LENGTH: 7
<212> TYPE: PRT
<213> ORGANISM: Artificial
<220> FEATURE:
<223> OTHER INFORMATION: Peptide linker

<400> SEQUENCE: 10

Leu Ala Phe Lys Leu Lys Leu
1               5

<210> SEQ ID NO 11
<211> LENGTH: 21
<212> TYPE: PRT
<213> ORGANISM: Artificial
<220> FEATURE:
<223> OTHER INFORMATION: Leader sequence

<400> SEQUENCE: 11

Met Lys Leu Pro Val Arg Leu Leu Val Leu Met Phe Trp Ile Pro Gly
1               5                   10                  15

Glu Glu Arg Gly Lys
            20

<210> SEQ ID NO 12
<211> LENGTH: 25
<212> TYPE: PRT
<213> ORGANISM: Artificial
<220> FEATURE:
<223> OTHER INFORMATION: Leader sequence

<400> SEQUENCE: 12

Met Gly Val Leu Leu Thr Gln Arg Thr Leu Leu Ser Leu Val Leu Ala
1               5                   10                  15

Leu Leu Phe Pro Ser Met Ala Ser Met
            20                  25
```

GLYCOPROTEIN VI FUSION PROTEINS

FIELD OF THE INVENTION

The present invention relates to Glycoprotein VI (GPVI) fusion proteins (GPVI-fusion proteins) comprising a tag like myc, GST, HA, FLAG, STREP but preferably a immunoglobulin molecule (Ig), more preferably a Fc portion of said Ig and a protein or oligopeptide having the biological activity of GPVI (GPVI-like protein) which is binding to collagen.

Procedures for production and purification of said fusion proteins are disclosed. Methods and kits for the screening of potential agonists or antagonists for GPVI-collagen and/or platelet-collagen interactions are provided.

The GPVI-fusion proteins are useful for the treatment of thrombotic and cardiovascular events and disorders related to GPVI-collagen and/or platelet-collagen interactions. Furthermore the fusion proteins are useful for coating natural or artificial surfaces in order to render them nonadhesive for cells and prevent the activation of cells.

BACKGROUND

The adhesion and activation of resting, circulating platelets at a site of vascular injury is the first step in a process leading to the formation of a thrombus, which is converted into a hemostatic plug. Collagen is one of the major components of the vessel wall responsible for platelet activation. Many types of collagen exist, and seven of these are found in the subendothelial layers. Several different receptors for collagen have been identified on platelets including CD36 (Matsuno, et al., Br. J. Haematol. 92, 960-967, 1996) and a p65 collagen type I specific receptor (Chiang et al., J. Clin. Invest. 100, 514-521, 1997), but the major ones are now considered to be integrin $\alpha_2\beta_1$ and the nonintegrin GPVI. It was determined about 20 years ago that GPVI is a major platelet glycoprotein with a molecular mass in the 60-65-kDa range and an acid pI (Clemetson et al., J. Clin. Invest. 70, 304-311, 1982) which forms a complex together with the Fcγ common subunit. The GPVI subunit contains the collagen binding site and the Fcγ subunit is responsible for signalling. The complex forms one of the major collagen receptors on the platelet surface, critical for platelet activation in response to collagen. Its role as a putative collagen receptor was established following the identification of a patient in Japan with a mild bleeding disorder whose platelets had a specific defect in response to collagen and lacked this receptor (Moroi et al., J. Clin. Invest. 84, 1440-1445, 1989). This patient had also developed autoantibodies to the deficient receptor, and these were used to characterize the molecule further (Sugiyama et al., Blood 69, 1712-1720, 1987). It was also demonstrated that the recognition sequence on collagen for GPVI is a repeated Gly-Pro-Hyp (Hyp=hydroxyproline) triplet within the collagen triple helical structure and that synthetic peptides based on this structure could be used as specific GPVI-directed agonists (Mortonet al., Thromb. Res. 72, 367-372, 1993). The GPVI/FCγ complex was shown to signal to the platelet interior by an immune receptor-like mechanism, involving activation of $p72^{syk}$ and leading by a cascade of kinase/phosphatase/adaptor protein interactions to activation of PLCγ2 and hence to release of granules and platelet aggregation.

Thus, it is clear from the prior art that GPVI-like proteins are very interesting compounds either as tool for the screening of potential agonists or antagonists of the GPVI-collagen interaction or as active principle.

In WO 00/68377 DNA coding for GPVI or biologically fragments thereof, recombinant human GPVI and pharmaceutical compositions thereof are disclosed. Further, the application describes the use of recombinant GPVI as a screening tool for detecting specific inhibitors or activators of platelet-collagen interactions. However, because of its transmembrane domain the recombinant protein is not secreted in the extracellular medium and so it is difficult to purify. Therefore the whole cells expressing this protein have to be used in a screening assay. Further, in view of GPVI as active agent, it is known that recombinant proteins often have a reduced circulating half-life, which leads to a need of frequent application of the drug and therefore results in high costs for the therapy.

Therefore, it was the goal of the present invention to provide molecules with the biological activity of GPVI having the following improved properties: high expression level in the host cell, secretion into the extracellular medium and easy purification, enhanced circulating half-life and, with respect to the use as screening tool, easy detectability by commercially available antibodies.

SUMMARY OF THE INVENTION

An object of the present invention is therefore to provide fusion proteins and their use as active agent and as screening tools for detecting specific inhibitors or activators of GPVI-collagen interaction and of platelet-collagen interactions.

Another object of the invention is to provide DNA molecules encoding said fusion proteins, vectors comprising said DNA molecules, host cells comprising said vectors and methods for producing said fusion proteins.

Another object of the invention is to provide kits and methods comprising such fusion proteins for the screening of agonists or antagonists of GPVI-collagen interaction and/or of platelet-collagen interactions.

A further object of the invention is to provide said fusion proteins for the use in the treatment of thrombotic and cardiovascular events and disorders related to GPVI-collagen interaction and/or to platelet-collagen interactions and medicaments and pharmaceutical packs comprising said fusion proteins.

A further object of the invention is to provide said fusion proteins for coating natural or artificial surfaces in order to render them nonadhesive for cells and prevent the activation of cells and for modifying intraocular lenses in order to lessen the thrombogenicity of the lens material.

Other objects of the present invention are apparent for a skilled person on the basis of the following detailed description.

These objects are achieved on the basis of the finding that fusion proteins comprising a tag like myc, GST, HA, FLAG, STREP, but preferably an Immunoglobulin molecule (Ig), more preferably a Fc portion of said Ig and a protein or oligopeptide having the biological activity of GPVI are expressed in high amounts in the host cells, are secreted in the extracellular medium and are therefore easy to purify. The disclosed molecules possess enhanced circulating half-life and are easily detectable by commercially available antibodies.

Due to their easy producibility they can be used for the screening of agonists or antagonists of GPVI-collagen and/or platelet-collagen interactions. Methods and kits for the screening of agonists and antagonists comprising a fusion protein as defined above and below are provided.

The fusion proteins of the present invention are useful in the prevention, prophylaxis, therapy and treatment of thrombotic and cardiovascular events and disorders related to GPVI-collagen and/or platelet-collagen interactions including increased platelet activation with collagen, such as atherosclerotic plaque rupture, unstable angina or, during surgical treatment such as percutaneous transluminal coronary angioplasty (PTCA). Pharmaceutical compositions comprising said fusion proteins for the treatment of thrombotic and cardiovascular events and disorders related to GPVI-collagen and/or platelet-collagen interactions are provided.

Furthermore, the fusion proteins can be used for coating natural or artificial surfaces coming in contact with body fluids, for example protheses, artificial organs, ocular lenses, sutures, artificial vascular segments, catheters, dialysers, tubes and vessels carrying blood, in order to render them nonadhesive for cells and prevent the activation of cells.

If artificial surfaces come in contact with blood, then there is increased tendency to induce thrombotic events by activation of platelets and/or induction of coagulation. These effects may cause failure of vascular grafts, cardiac valves, stents, catheters or any other blood contacting device or material. The ability of the fusion proteins disclosed here to create non-thrombogenic surfaces may therefore be further exploited by immobilization of this fusion proteins to the materials and devices described above. Such a treatment should render such materials or devices biocompatible and thromboresistant.

DETAILED DESCRIPTION

Fusion proteins are known in the art. For example, fusion proteins may effectively block a proteolytic enzyme from physical contact with the protein backbone itself, and thus prevent degradation. Additional advantages include, under certain circumstances, improved yield in a specific expression system, secretion in the extracellular medium, easy purification, correct folding of a target protein, and increasing the stability, circulation time, and the biological activity of the therapeutic protein.

One such modification is the use of the Fc region of immunoglobulins. Antibodies comprise two functionally independent parts, a variable domain known as "Fab", which binds antigen, and a constant domain, known as "Fc" which provides the link to effector functions such as complement or phagocytic cells.

The Fc portion of an immunoglobulin mediates a long plasma half life when fused to certain proteins that have particularly short half lives, whereas the mere Fab fragment is short-lived (Capon et al., Nature, 337: 525-531, 1989). For example, IL-10, an anti-inflammatory and anti-rejection agent has been fused to the N-terminus of murine Fcγ2a in order to increase the cytokine's short circulating half-life (Zheng, X. et: al., The Journal of Immunology, 154: 5590-5600, 1995). In addition, the N-terminus of interleukin 2 has also been fused to the Fc portion of IgG1 or IgG3 to overcome the short half life of interleukin 2 and its systemic toxicity (Harvill et al., Immunotechnology, 1: 95-105, 1995).

Therapeutic and analytic fusion proteins have also been constructed using the Fc domain to incorporate functions such as Fc receptor binding, protein A binding, complement fixation and placental transfer which all reside in the Fc proteins of immunoglobulins. For example, the Fc region of an IgG1 antibody has been fused to the N-terminal end of CD30-L, a molecule which binds CD30 receptors expressed on Hodgkin's Disease tumor cells, anaplastic lymphoma cells, T-cell leukemia cells and other malignant cell types (U.S. Pat. No. 5,480,981). Furthermore, it has been reported in 1996 that efficient expression and secretion of certain non-mutant target proteins can be achieved by expression of fusion proteins comprising an Fc portion of an Ig and said target proteins followed by proteolytic cleavage of the target protein (WO 96/08570; U.S. Pat. No. 5,541,087).

The present invention discloses novel fusion proteins having GPVI-like activity in their ability to bind to collagen, but with additional advantageous properties such as improved yield, secretion in the extracellular medium, easy purification, long serum half-life and easy detectability. Therefore, GPVI-fusion proteins can be easily used for screening purposes. The molecules of the present invention can be used in a lot of standard screening assays like ELISA, SPA, SPR, Filter-assay and homogeneous assays. They are easily detectable by commercially available antibodies.

These novel fusion proteins comprise essentially a tag like myc, GST, HA, FLAG, STREP but preferably an Ig, more preferably a Fc portion of said Ig and a GPVI-like protein, wherein the portion of the fusion protein having the activity of GPVI may be altered in its glycosylation pattern, or may be different from the human GPVI with respect to its amino acid sequence (e.g. mutated or truncated). Also the immunoglobulin portion, preferably a Fc portion of an Ig, may be modified or mutated having for example a reduced affinity to Fc receptors.

So, it is an object of the present invention to provide a fusion protein with GPVI-like activity having the above described improved properties, wherein said fusion protein comprises a tag like myc, GST, HA, FLAG, STREP but preferably an Ig molecule like a whole antibody, an Ig heavy or light chain or a fragment of the heavy chain (e.g. a $C_H$ or Fc portion) and an GPVI-like protein, wherein said tag or Ig moiety is fused covalently directly or indirectly (via a linker molecule) to said GPVI-like protein, and the Ig portion and/or the GPVI portion may be modified or mutated, selected from the group:

(I) $H_2N$-tag-GPVI-COOH
(II) $H_2N$-tag-L-GPVI-COOH
(III) $H_2N$-tag-GPVI$_m$-COOH
(IV) $H_2N$-tag$_m$-GPVI-COOH
(V) $H_2N$-tag$_m$-GPVI$_m$-COOH
(VI) $H_2N$-tag$_m$-L-GPVI-COOH
(VII) $H_2N$-tag-L-GPVI$_m$-COOH
(VIII) $H_2N$-tag-GPVI$_{trunc}$-COOH
(IX) $H_2N$-tag-L-GPVI$_{trunc}$-COOH
(X) $H_2N$-GPVI-tag-COOH
(XI) $H_2N$-GPVI-L-tag-COOH
(XII) $H_2N$-GPVI$_m$-tag-COOH
(XIII) $H_2N$-GPVI-tag$_m$-COOH
(XIV) $H_2N$-GPVI$_m$-tag$_m$-COOH
(XV) $H_2N$-GPVI-L-tag$_m$-COOH
(XVI) $H_2N$-GPVI$_m$-L-tag-COOH
(XVII) $H_2N$-GPVI$_{trunc}$-tag-COOH
(XVI II) $H_2N$-GPVI$_{trunc}$-L-tag-COOH Herein GPVI has the meaning of naturally occurring GPVI from mammalian, preferably human origin, and includes also recombinant GPVI engineered from natural sources.

GPVI$_{trunc}$ is an GPVI according to this invention which is truncated but not mutated in its amino acid sequence. Truncated forms are protein fragments having essentially the full or a reduced biological activity of GPVI. A preferred truncated form of GPVI according to this invention is the soluble extracellular domain of GPVI containing the collagen binding site which can prevent platelet activation by collagen. An especially preferred truncated form is the part of the extracellular domain of human mature GPVI as described in WO 00/68377 beginning with amino acid glutamine at position 21 and ending with amino acid asparagine at position 269, amino acids 253-501 of SEQ ID NO: 1 or amino acids 33-281 of SEQ ID NO: 2.

GPVI$_m$ is an GPVI according to this invention which is mutated but not truncated in its amino acid sequence. The number of mutations is not limited but is restricted to the loss of the biological activity of the molecule. GPVI, GPVI$_m$, GPVI$_{trunc}$ according to the invention is glycosylated, non-glycosylated, partially glycosylated or otherwise modified in its glycosylation pattern.

Herein, tag has the meaning of any peptide or protein which can be fused to GPVI and used for identification of GPVI like myc, GST, HA, FLAG, STREP, but preferably it has the meaning of a Ig molecule like a whole antibody, an Ig heavy or light chain or a fragment of the heavy chain (e.g. a C$_H$ or Fc portion). More preferably the Fc portion of an Ig, for example the Fc of IgG1, IgG2, IgG3, IgG4, IgD, IgM, IgA, lambda or kappa, or an analog or fragment thereof is used.

Herein myc, GST, HA, FLAG and STREP has the meaning of the well-defined peptides c-myc epitope-tag, HA-tag (hemagglutin tag), Flag-epitope-tag (leader peptide of the gene-10 product from bacteriophage T7 or a fragment thereof and STREP-tag (a short peptide with high affinity for streptavidin). GST has the meaning of glutathione-S-transferase.

The Fc region of an immunoglobulin is the carboxyl-terminal portion of an immunoglobulin heavy chain constant region. The Fc regions are particularly important in determining the biological functions of the immunoglobulin and these biological functions are termed effector functions. As known, the heavy chains of the immunoglobulin subclasses comprise four or five domains: IgM has five heavy chain domains, and IgA, IgD and IgG have four heavy chain domains. The Fc region of IgA, IgD and IgG is a dimer of the hinge-CH$_2$—CH$_3$ domains, and in IgM it is at least a dimer of the hinge-CH$_2$—CH$_3$—CH$_4$ domains (see, W. E. Paul, ed., 1993, Fundamental Immunology, Raven Press, New York, N.Y.).

The Fc region according to this invention can be joined at its amino-terminus by a peptide bond to the carboxy-terminal amino acid of the GPVI-like protein (GPVI-FC), or it may be linked at its carboxy-terminus by a peptide bond to the amino-terminal amino acid of the GPVI-like protein (Fc-GPVI).

In a especially preferred embodiment of the invention the GPVI-fusion protein comprises a Fc portion of an IgG, and the extracellular domain of human mature GPVI beginning with amino acid glutamine at position 21 and ending with amino acid asparagine at position 269 (see SEQ. I and II) binding to collagen with high affinity.

Using the Fc portion, the molecule can easily be purified using protein A affinity columns. Using a tag like myc, GST, HA, FLAG or STREP the fusion protein may be purified by affinity purification with glutathione or biotin, or in case of myc, HA or FLAG with antibodies directed against this domanis. Furthermore the fusion proteins of the present invention can be detected easily by commercially available antibodies, which are directed against these portions and bear a detectable label e.g. alkaline phosphatase, peroxidase, glucose oxidase, 7-amino-4-methyl-coumarin-3-acetic acid (AMCA), fluorescein isothiocyanate (FITC), phycoerythrin, biotin or a radioactive marker. Such antibodies are available for example from ICN Biomedicals GmbH, Germany.

Therefore, a screening assay for potential agonists or antagonists for GPVI-collagen and/or platelet-collagen interactions can easily established with such fusion proteins.

With regard to the use of the GPVI-fusion proteins as active agent, it is known that the Fc portion of an immunoglobulin mediates a long plasma half-life when fused to proteins having particularly short half-lives (Capon, et al., Nature 337: 525-531, 1989). For example, the N-terminus of interleukin 2 has also been fused to the Fc portion of IgG1 or IgG3 to overcome the short half life of interleukin 2 and its systemic toxicity (Harvill et al., Immunotechnology, 1: 95-105, 1995).

Further enhancement of the in vivo circulating half-life of an IgG1 or IgG3 fusion protein may be obtained by introducing a genetic modification of one or more amino acid in the constant region of the IgG1 or IgG3 heavy chains that reduces the binding affinity of these isotypes for Fc receptors (WO 99/43713). Such modifications are, first introducing a mutation, deletion, or insertion in the IgG1 constant region at one or more amino acids selected from Leu$_{234}$ Leu$_{235}$, Gly$_{236}$, Gly$_{237}$, Asn$_{297}$ and Pro$_{331}$, and then linking the resulting Ig, or portion thereof, to the GPVI-like protein. In case of the IgG3, the mutation, deletion, or insertion may be introduced at one or more amino acids selected from Leu$_{281}$, Leu$_{282}$, Gly$_{283}$, Gly$_{284}$, Asn$_{344}$, and Pro$_{378}$, and the resulting immuno-globulin, or portion thereof, is linked to the GPVI-like protein.

In another embodiment of the invention the plasma half-life of the antibody-based fusion protein can be enhanced by using IgG2 or IgG4 Fc-portions which have reduced or no binding affinity for Fc receptors.

The important sequences for the binding of IgG to the Fc receptors have been reported to be located in the CH2 domain. Therefore such fusion proteins may be obtained by linking at least the CH2 domain of the IgG molecule to the GPVI-like protein.

Thus, in the case where tag means an Ig, tag$_m$ is an Ig, preferably a Fc fragment, as defined above which is mutated in its amino acid sequence and/or modified in its glycosylation pattern.

The tag molecule and the GPVI-like protein according to this invention may also be linked by linker molecules, wherein the chemical or amino acid linkers are of varying length. The chemical linkers are well known in the art. Peptide linkers are preferred.

The peptide linker (L) often is a series of peptides such as. e.g., glycine andlor serine. Amino acid linkers which may be used include the following sequences:
1. Ala Ala Ala
2. Ala Ala Ala Ala (SEQ ID NO: 3),
3. Ala Ala Ala Ala Ala (SEQ ID NO: 4),
4. Ser,
5. Ser Ser,
6. Gly Gly Gly,
7. Gly Gly Gly Gly (SEQ ID NO: 5),
8. Gly Gly Gly Gly Gly (SEQ ID NO: 6),
9. Gly Gly Gly Gly Gly Gly Gly (SEQ ID NO: 7),
10. Gly Pro Gly,
11. Gly Gly Pro Gly Gly (SEQ ID NO: 8),
12. Gly Gly Gly Gly Ser (SEQ ID NO: 9),
13. Ser Pro Gly,
14. Cys Gly Arg
15. Leu Ala Phe Lys Leu Lys Leu (SEQ ID NO: 10)
16. any combinations of subparts 1-14

Preferred amino acid linkers are
(Gly-Gly-Gly-Gly-Ser)$_x$ wherein x is 1-5 (SEQ ID NO: 13),
Ser-Pro-Gly,
Cys-Gly-Arg and
Leu-Ala-Phe-Lys-Leu-Lys-Leu (SEQ ID NO: 14).

Additional suitable linkers are disclosed in Robinson et al. (Proc. Natl. Acad. Sci. USA; 95, 5929, 1998).

Thus, the invention presents novel GPVI-fusion proteins, preferably Fc-fusion proteins which have significant advantages over corresponding natural forms of GPVI which are improved yield, secretion in the extracellular medium, easy purification, for example, on a protein A column, longer serum half-life and easy detectability by commercially available antibodies.

The invention also relates to a DNA molecule that encodes any of the fusion proteins disclosed above and depicted in the claims.

As a preferred embodiment a DNA molecule is disclosed that encodes a fusion protein as defined above and in the claims comprising:
(a) leader sequence
(b) a Fc region of an Ig molecule
(c) a target protein sequence having the biological activity of GPVI.

The leader sequence of the invention as indicated above is a polynucleotide which encodes an leader amino acid sequence that initiates transport of a protein across the membrane of the endoplasmic reticulum. Leader sequences which will be useful in the invention include antibody light chain signal sequences, e.g., antibody 14.18 (Gillies et. al., Jour. of Immunol. Meth., 125:191, 1989), antibody heavy chain signal sequences, e.g., the MOPC141 antibody heavy chain signal sequence (Sakano et al., *Nature* 286:5774, 1980), and any other signal sequences which are known in the art (see for example, Watson, Nucleic Acids Research 12:5145, 1984). Each of these references is incorporated herein by reference. Leader sequences have been well characterized in the art and are known typically to contain 16 to 30 amino acid residues, and may contain greater or fewer amino acid residues. A typical leader peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide is usually cleaved within the lumen of the endoplasmic reticulum by cellular enzymes known as signal peptidases. Preferred polynucleotide leader sequences encode for the peptides having the amino acid sequence Met-Lys-Leu-Pro-Val-Arg-Leu-Leu-Val-Leu-Met-
Phe-Trp-Ile-Pro-Gly-Glu-Glu-Arg-Gly-Lys(See SEQ ID NO: 11)

or

Met-Gly-Val-Leu-Leu-Thr-Gln-Arg-Thr-Leu-Leu-Ser-
Leu-Val-Leu-Ala-Leu-Leu-Phe-Pro-Ser-Met-
Ala-Ser-Met (See SEQ ID NO: 12).

Potential cleavage sites of the leader peptide generally follow the "(−3, −1) rule". Thus a typical leader peptide has small, neutral amino acid residues in positions −1 and −3 and lacks proline residues in this region. The signal peptidase will cleave such a signal peptide between the −1 and +1 amino acids. Thus, the portion of the DNA encoding the leader sequence may be cleaved from the amino-terminus of the fusion protein during secretion. This results in the secretion of a fusion protein consisting of the Ig region and the GPVI-like protein. A detailed discussion of signal peptide sequences is provided by von Heijne (Nucleic Acids Res., 14:4683, 1986). As would be apparent to one of skill in the art, the suitability of a particular leader sequence for use in a secretion cassette may require some routine experimentation. A leader sequence is also referred to as a "signal peptide", "signal sequence" or "leader peptides" and each of these terms having meanings synonymous to signal sequence may be used herein.

The leader sequence and the GPVI-like protein respectively the tag molecule according to this invention may also be linked by linker molecules as defined above The invention also relates to expression vectors comprising said DNA molecules which promote expression of the GPVI-fusion protein.

As used herein, "vector" means any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include Baculo, a retrovirus, an adenovirus and an adeno-associated virus. As used herein, "expression of a target protein" is understood to mean the transcription of the DNA sequence, translation of the mRNA transcript, and secretion of a protein product that is folded into a correct, active conformation.

According to the invention eukaryotic, preferably mammalian, host cells are used that are suitable for expressing a fusion protein as defined in this application. Methods of transfecting such host cells with said vector, expressing, purifying and isolating the fusion proteins of this invention are well known in the art.

Therefore, the method for producing the fusion proteins according to this invention comprises:
a) constructing a DNA encoding a fusion protein that comprises optionally a leader sequence for secretion, the tag or Ig molecule, the GPVI-like protein and optionally linker-sequences,
b) placing said fused DNA in an appropriate expression vector,
c) expressing said fusion protein in a eukaryotic cell, and
d) purifying said secreted fusion protein.

The present invention furthermore provides a method of screening for agonists or antagonists of the GPVI-collagen binding by observing the binding or stimulation or inhibition of a functional response.

For example the screening method may comprise the following steps:
a) contacting a collagen coated surface with the fusion protein according to the present invention and a potential antagonists or agonists of GPVI-collagen and/or platelet-collagen interaction under conditions which ensure the binding of said fusion protein to the collagen coated surface in the absence of the antagonist or agonist,
b) contacting the collagen bound fusion protein with an antibody comprising a recognition site with binding affinity to the fusion protein and a detectable label under conditions which ensure the binding of the antibody to the fusion protein without affecting the binding of the fusion protein to the collagen coated surface,
c) performing a detection step to detect the remaining fusion protein bound to collagen.

The present invention provides furthermore a kit containing components for screening for agonists or antagonists of GPVI-collagen and/or platelet-collagen interaction:
These may be:
a) a fusion protein as defined above and below
b) a detectable label bearing second antibody directed against the tag/Ig portion of the fusion protein
c) a collagen coated surface
d) suitable buffers (e.g. phosphate, carbonate or HEPES-buffer)

The invention also relates to medicaments comprising at least one GPVI-fusion protein as defined above and below as active agent, preferably a Fc-GPVI fusion protein, optionally together with pharmaceutically acceptable carriers, diluents, and excipients. These medicaments may contain other active agents that are helpful in treatment of thrombotic and cardiovascular events and disorders related to platelet-collagen interactions including increased platelet activation with collagen, such as atherosclerotic plaque rupture, unstable angina or, during surgical treatment such as percutaneous transluminal coronary angioplasty (PTCA). Preferred additional active agents are aspirin, heparin, saratin or streptokinase or a combination thereof.

The present invention furthermore provides pharmaceutical packs comprising a medicament comprising a GPVI-fusion protein as defined above and below as a active agent and a medicament comprising aspirin, heparin, saratin or streptokinase or a combination thereof for joined or timely shifted administration.

Such medicaments and pharmaceutical packs may be for parenteral administration, or for oral, pulmonary, nasal, transdermal or other forms of administration. In general, comprehended by the invention are medicaments comprising effective amounts of protein or derivative products of the invention optionally together with pharmaceutically acceptable carriers or excipients.

The term "parenteral" includes herein subcutaneous, intravenous, intraarticular and intratracheal injection and infusion techniques. Parenteral compositions and combinations are most preferably administered intravenously either in a bolus form or as a constant fusion according to known procedures.

As used herein, the term "pharmaceutically acceptable carrier or excipient" means inert, non toxic liquid fillers, additives such as detergents, diluents of various buffer content (e.g., Tris-HCl, acetate, phosphate), pH and ionic strength, preservatives (e.g., Thimersol, benzyl alcohol), solubilizers (e.g., Tween 80, Polysorbate 80), emulsifiers, adjuvants, antioxidants (e.g., ascorbic acid, sodium metabisulfite), solvents or solutions and bulking substances (e.g., lactose, mannitol) not reacting adversely with the active compounds or with the patient.

Suitable liquid carriers are well known in the art such as steril water, saline, aqueous dextrose, sugar solutions, ethanol, glycols and oils, including those of petroleum, animal, vegetable, or synthetic origin, for example, peanut oil, soybean oil and mineral oil.

Topical applications may be in the form of aqueous or oily suspensions, solutions, emulsions, jellies or preferably emulsion ointments.

With respect to said suitable formulations it should be pointed out that the fusion proteins of the present invention may eventually form pharmaceutically acceptable salts with any non-toxic, organic or inorganic acid showing changed solubility. Inorganic acids are, for example, hydrochloric, hydrobromic, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic, benzoic, phenylacetic, cinnamic, salicylic and sulfonic acids. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, light metals of group IIIA including aluminium and organic primary, secondary and tertiary amines such as trialkylamines including triethylamine, procaine, dibenzylamine, 1-ethenamine, N,N'-dibenzylethylene-diamine, dihydroabietylamine and N-alkylpiperidine.

The effective dosages may be determined using diagnostic tools which are known in the prior art. In general, the optimum therapeutically acceptable dosage and dose rate for a given patient within the above-said ranges depends on a variety of factors, such as the activity of the specific active material employed, the age, body weight, general health, sex, diet, time and route of administration, rate of clearance or the object of treatment, i.e. therapy or prophylaxis and the nature of the thrombotic disease to be treated. One skilled in the art will be able to ascertain effective dosages by administration and observing the desired therapeutic effect. The dosages may also vary over the course of therapy, with a relatively high dosage being used initially, until therapeutic benefit is seen, and lower dosages used to maintain the therapeutic benefits.

This invention also provides an implantable or extracorporal medical device for use in contact with body fluids in order to render the device surface substantially thromboresistant, coated with an immobilized polypeptide as defined above and in the claims. The polypeptide according to the invention is immobilzed on a medical device so as to render the surface biocompatible and thromboresistant. Such devices sometimes have surfaces properties which typically induce platelet aggregation, which is a disadvantage in their intended uses in inplantable and extracorporeal devices in contact with blood or other body fluids. Examples for such devices which are commonly made from plastics materials and synthetic fibres are protheses, artificial organs, ocular lenses, sutures, artificial vascular segments, catheters, dialysers, tubes and vessels carrying blood.

Posterior capsule opacification (PCO) is a common complication after cateract extraxtion, despite the modern surgical techinques and lenses which are used for this procedure. PCO is caused by the proliferation and migration of lens epithelial cells across the posterior capsule thus reducing the visual acuity. Physical treatments as well as chemically modified lenses have been proposed to reduce formation of PCO. Heparin lens coating or topical heparin eyedrops have been used to reduce PCO, indicating that thrombogenic mechanisms are involved in the formation of PCO. Therefore the fusion proteins disclosed of the present invention may be used to reduce or prevent PCO.

Figure 1:
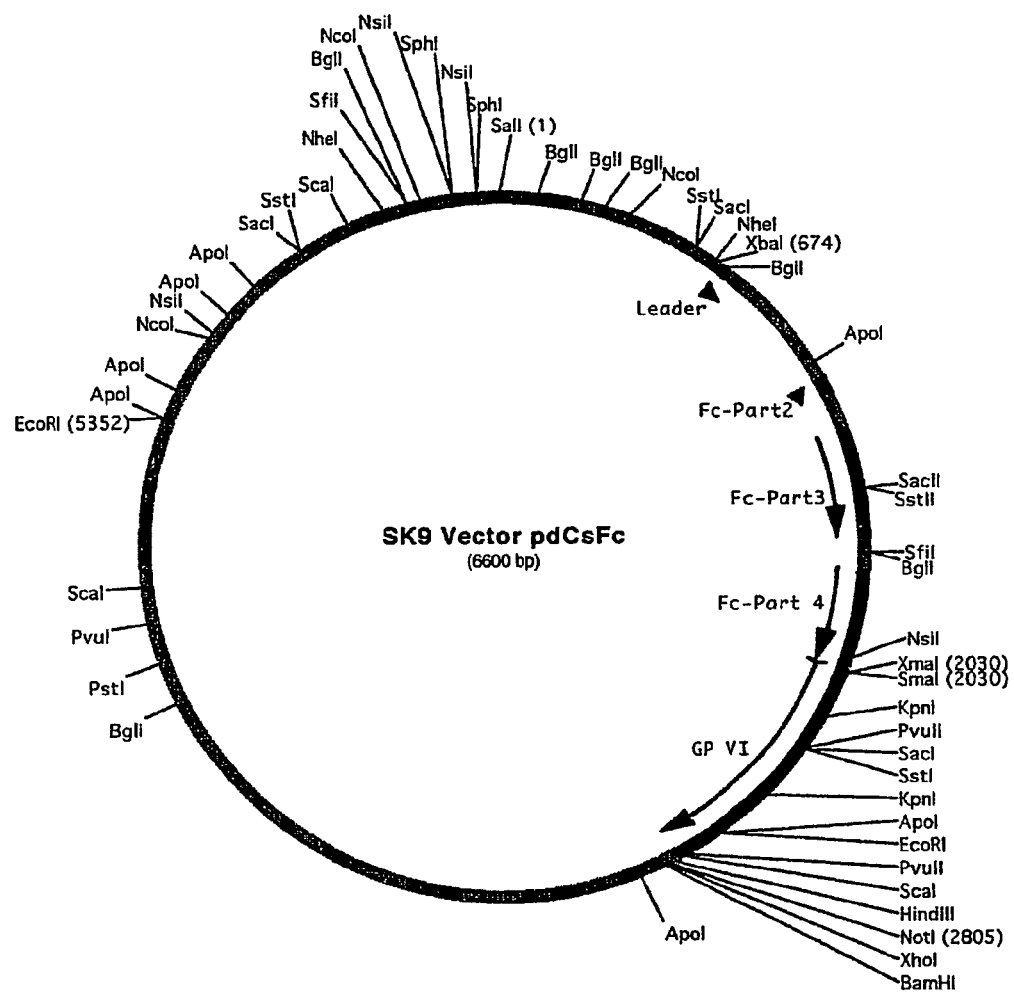
FIG. 1.
Figure 2:
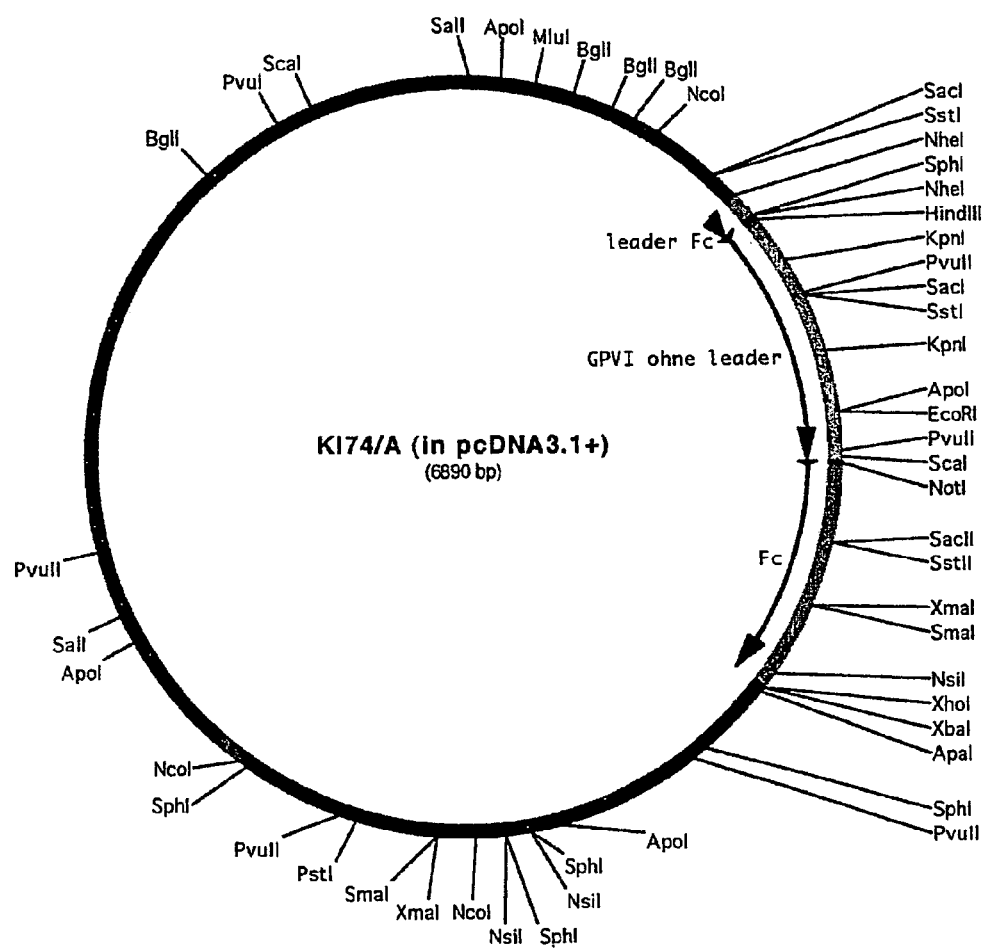
Figure 3:
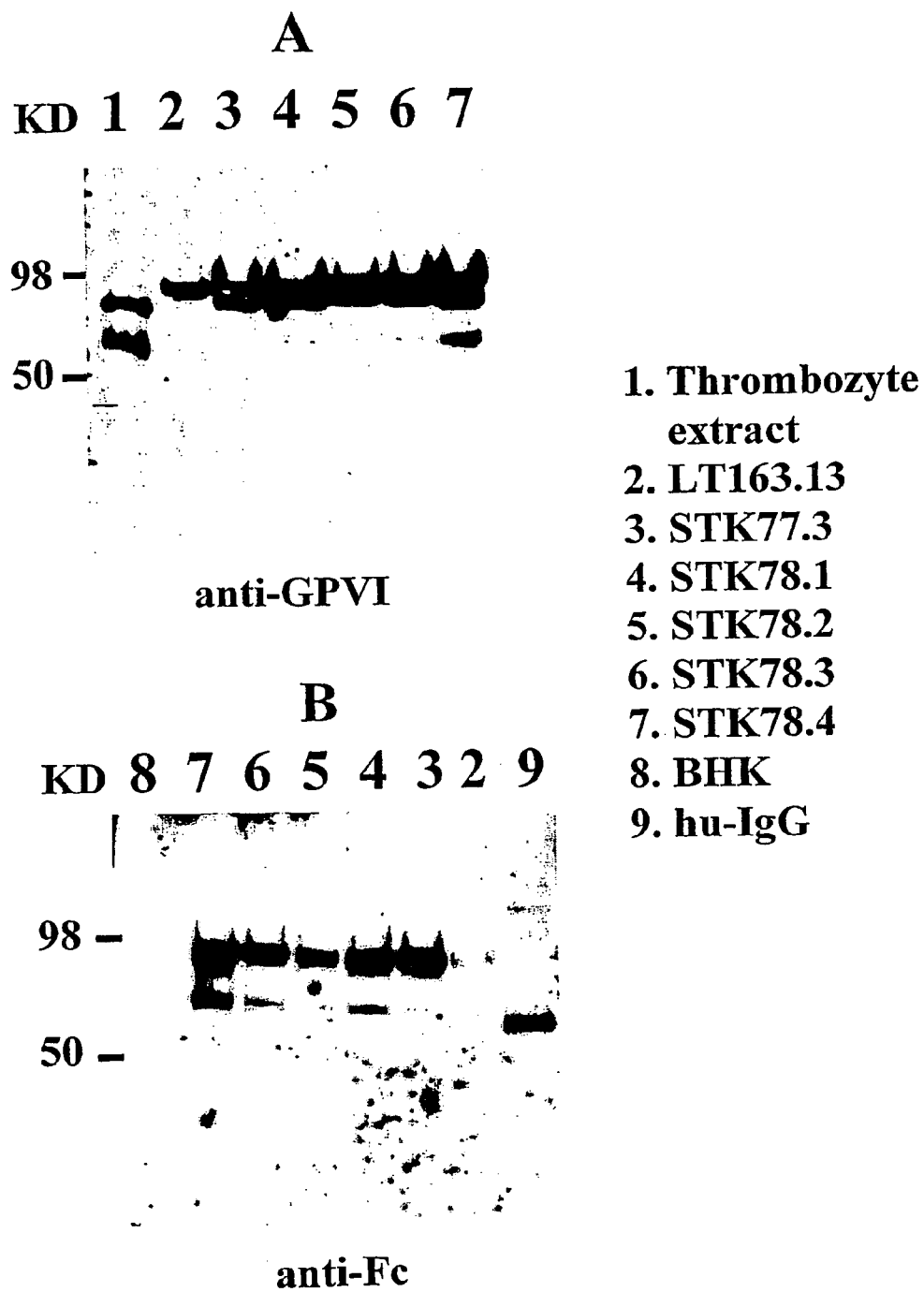

Vector map of SK9 coding for Fc-GPVI.

FIG. 2:

Vector map of KL74 coding for GPVI-Fc.

FIG. 3:

Western blot analysis of Fc-GPVI protein as described in the examples. After SDS gel electrophoresis on a 10% acrylamid gel the fusion protein was detected either with a polyclonal anti GP VI antiserum (A) or a polyclonal anti Fc IgG fraction (B). As a positive control probe was used an extract from thrombozytes (1) for blot A and a hu-IgG antibody for blot B.

As a negative control supernatant of BHK cells was used. The probes 2-7 are represent different clones from 2 different transfection experiments. The band with a size of about 90 KD is complete Fc-GPVI.

FIG. 4:

GPVI-Fc binding at collagen.

GPVI-Fc, solved in HEPES buffer (pH 7.4) containing 1% BSA and 0.05% Tween 20, was allowed to bind at collagen-coated microtiter plates. The amount of collagen-bound GPVI-Fc was calorimetrically detected by an anti-Fc antibody conjugated with horse radish peroxidase. Non-specific binding was estimated by a collagen non-specific Fc fusion protein applied instead of GPVI-Fc. Data shown as mean (n=2).

FIG. 5:

Inhibition of GPVI-Fc binding by GPVI-specific antagonists.

Binding of GPVI-Fc was carried out in the presence of collagen related peptides (CRP) and anti-GPVI serum, respectively. CRP mimic the collagen binding domain that uniquely mediates binding between the GPVI receptor and collagen. Because of the competition between CRP and collagen for GPVI-Fc, the amount of collagen-bound GPVI-Fc decrease with increasing CRP concentration. Inhibition of GPVI-Fc binding could be demonstrated with an anti-GPVI serum obtained from rabbits immunized with GPVI receptor protein that was prepared from human platelets. Because the titer of anti-GPVI antibodies was not determined within the serum, the serum dilution is depicted. Data are shown as mean (n=2).

FIG. 6:

Suppression of collagen-induced platelet aggregation by GPVI-Fc.

Platelet aggregation is turbidometrically determined after the addition of 10 μg/ml collagen (control) and in the presence of different GPVI-Fc concentrations. Data are shown as means (n=4).

FIG. 7:

Sensorgram for the interaction of GPVI with the collagen surface.

Collagen type III (human) was coupled to the sensor surface as mentioned in the methods and GPVI was passed over the surface with concentrations ranging from 0.2 μg/ml to 50 μg/ml.

FIG. 8:

Plot of the equilibrium binding data versus protein concentration of GPVI.

SEQUENCE INFORMATION

---

SEQ ID NO:1
Sequence of the Fc-GPVI fusion protein (inclusive leader sequence) as encoded in SK9.

――――Leader-Sequence――――
Met Lys Leu Pro Val Arg Leu Leu Val Leu Met Phe Trp Ile Pro Gly
1            5              10             15

―――┐┌―― Fc-Portion ――
Glu Glu Arg Gly Lys Glu Pro Lys Ser Ser Asp Lys Thr His Thr Cys
          20                25              30

―――― Fc-Portion ――――
Pro Pro Cys Pro Ala Pro Glu Leu Leu Gly Gly Pro Ser Val Phe Leu
      35              40              45

―――― Fc-Portion ――――
Phe Pro Pro Lys Pro Lys Asp Thr Leu Met Ile Ser Arg Thr Pro Glu
      50              55              60

―――― Fc-Portion ――――
Val Thr Cys Val Val Val Asp Val Ser His Glu Asp Pro Glu Val Lys
65            70              75              80

―――― Fc-Portion ――――
Phe Asn Trp Tyr Val Asp Gly Val Glu Val His Asn Ala Lys Thr Lys
          85              90              95

―――― Fc-Portion ――――
Pro Arg Glu Glu Gln Tyr Asn Ser Thr Tyr Arg Val Val Ser Val Leu
          100             105             110

―――― Fc-Portion ――――
Thr Val Leu His Gln Asp Trp Leu Asn Gly Lys Glu Tyr Lys Cys Lys
          115             120             125

―――― Fc-Portion ――――
Val Ser Asn Lys Ala Leu Pro Ala Pro Ile Glu Lys Thr Ile Ser Lys
          130             135             140

―――― Fc-Portion ――――
Ala Lys Gly Gln Pro Arg Glu Pro Gln Val Tyr Thr Leu Pro Pro Ser
145             150             155             160

―――― Fc-Portion ――――
Arg Glu Glu Met Thr Lys Asn Gln Val Ser Leu Thr Cys Leu Val Lys
          165             170             175

―――― Fc-Portion ――――
Gly Phe Tyr Pro Ser Asp Ile Ala Val Glu Trp Glu Ser Asn Gly Gln
          180             185             190

―――― Fc-Portion ――――
Pro Glu Asn Asn Tyr Lys Thr Thr Pro Pro Val Leu Asp Ser Asp Gly
          195             200             205

―――― Fc-Portion ――――
Ser Phe Phe Leu Tyr Ser Lys Leu Thr Val Asp Lys Ser Arg Trp Gln
          210             215             220

―――― Fc-Portion ――――
Gln Gly Asn Val Phe Ser Cys Ser Val Met His Glu Ala Leu His Asn
          225             230             235             240

――― Fc-Portion ―――┐┌―Linker―┐┌―
His Tyr Thr Gln Lys Ser Leu Ser Leu Ser Pro Gly Gln Ser Gly Pro
          245             250             255

―――― Glycoprotein VI ――――
Leu Pro Lys Pro Ser Leu Gln Ala Leu Pro Ser Ser Leu Val Pro Leu
          260             265             270

―――― Glycoprotein VI ――――
Glu Lys Pro Val Thr Leu Arg Cys Gln Gly Pro Pro Gly Val Asp Leu
          275             280             285

―――― Glycoprotein VI ――――
Tyr Arg Leu Glu Lys Leu Ser Ser Ser Arg Tyr Gln Asp Gln Ala Val
          290             295             300

―――― Glycoprotein VI ――――
Leu Phe Ile Pro Ala Met Lys Arg Ser Leu Ala Gly Arg Tyr Arg Cys
305             310             315             350

―――― Glycoprotein VI ――――
Ser Tyr Gln Asn Gly Ser Leu Trp Ser Leu Pro Ser Asp Gln Leu Glu
          325             330             335

―――― Glycoprotein VI ――――
Leu Val Ala Thr Gly Val Phe Ala Lys Pro Ser Leu Ser Ala Gln Pro
          340             345             350

―――― Glycoprotein VI ――――
Gly Pro Ala Val Ser Ser Gly Gly Asp Val Thr Leu Gln Cys Gln Thr
          355             360             365

GlycoproteinVI
Arg Tyr Gly Phe Asp Gln Phe Ala Leu Tyr Lys Glu Gly Asp Pro Ala
    370             375             380

GlycoproteinVI
Pro Tyr Lys Asn Pro Glu Arg Trp Tyr Arg Ala Ser Phe Pro Ile Ile
385             390             395             400

GlycoproteinVI
Thr Val Thr Ala Ala His Ser Gly Thr Tyr Arg Cys Tyr Ser Phe Ser
            405             410             415

GlycoproteinVI
Ser Arg Asp Pro Tyr Leu Trp Ser Ala Pro Ser Asp Pro Leu Glu Leu
        420             425             430

GlycoproteinVI
Val Val Thr Gly Thr Ser Val Thr Pro Ser Arg Leu Pro Thr Glu Pro
        435             440             445

GlycoproteinVI
Pro Ser Ser Val Ala Glu Phe Ser Glu Ala Thr Ala Glu Leu Thr Val
    450             455             460

GlycoproteinVI
Ser Phe Thr Asn Lys Val Phe Thr Thr Glu Thr Ser Arg Ser Ile Thr
465             470             475             480

GlycoproteinVI
Thr Ser Pro Lys Glu Ser Asp Ser Pro Ala Gly Pro Ala Arg Gln Tyr
            485             490             495

GlycoproteinVI
Tyr Thr Lys Gly Asn
            500

SEQ ID NO:2
Sequence of the GPVI-Fc fusion protein (inclusive leader sequence) as encoded in KL74A Leader-Sequence
Met Gly Val Leu Leu Thr Gln Arg Thr Leu Leu Ser Leu Val Leu Ala
1               5               10              15

Linker
Leu Leu Phe Pro Ser Met Ala Ser Met Leu Ala Phe Lys Leu Lys Leu
            20              25              30

GlycoproteinVI
Gln Ser Gly Pro Leu Pro Lys Pro Ser Leu Gln Ala Leu Pro Ser Ser
        35              40              45

GlycoproteinVI
Leu Val Pro Leu Glu Lys Pro Val Thr Leu Arg Cys Gln Gly Pro Pro
        50              55              60

GlycoproteinVI
Gly Val Asp Leu Tyr Arg Leu Glu Lys Leu Ser Ser Ser Arg Tyr Gln
65              70              75              80

GlycoproteinVI
Asp Gln Ala Val Leu Phe Ile Pro Ala Met Lys Arg Ser Leu Ala Gly
            85              90              95

GlycoproteinVI
Arg Tyr Arg Cys Ser Tyr Gln Asn Gly Ser Leu Trp Ser Leu Pro Ser
            100             105             110

GlycoproteinVI
Asp Gln Leu Glu Leu Val Ala Thr Gly Val Phe Ala Lys Pro Ser Leu
            115             120             125

GlycoproteinVI
Ser Ala Gln Pro Gly Pro Ala Val Ser Ser Gly Gly Asp Val Thr Leu
    130             135             140

GlycoproteinVI
Gln Cys Gln Thr Arg Tyr Gly Phe Asp Gln Phe Ala Leu Tyr Lys Glu
145             150             155             160

GlycoproteinVI
Gly Asp Pro Ala Pro Tyr Lys Asn Pro Glu Arg Trp Tyr Arg Ala Ser
            165             170             175

GlycoproteinVI
Phe Pro Ile Ile Thr Val Thr Ala Ala His Ser Gly Thr Tyr Arg Cys
        180             185             190

GlycoproteinVI
Tyr Ser Phe Ser Ser Arg Asp Pro Tyr Leu Trp Ser Ala Pro Ser Asp
            195             200             205

GlycoproteinVI
Pro Leu Glu Leu Val Val Thr Gly Thr Ser Val Thr Pro Ser Arg Leu
    210             215             220

GlycoproteinVI
Pro Thr Glu Pro Pro Ser Ser Val Ala Glu Phe Ser Glu Ala Thr Ala
225             230             235             240

GlycoproteinVI
Glu Leu Thr Val Ser Phe Thr Asn Lys Val Phe Thr Thr Glu Thr Ser
            245             250             255

GlycoproteinVI
Arg Ser Ile Thr Thr Ser Pro Lys Glu Ser Asp Ser Pro Ala Gly Pro
            260             265             270

GlycoproteinVI                    Linker
Ala Arg Gln Tyr Tyr Thr Lys Gly Asn Cys Gly Arg Glu Pro Lys Ser
    275             280             285

Fc-Portion
Ser Asp Lys Thr His Thr Ser Pro Pro Ser Pro Ala Pro Glu Leu Leu
        290             295             300

Fc-Portion
Gly Gly Ser Ser Val Phe Leu Phe Pro Pro Lys Pro Lys Asp Thr Leu
305             310             315             320

Fc-Portion
Met Ile Ser Arg Thr Pro Glu Val Thr Cys Val Val Val Asp Val Ser
            325             330             335

Fc-Portion
His Glu Asp Pro Glu Val Lys Phe Asn Trp Tyr Val Asp Gly Val Glu
            340             345             350

Fc-Portion
Val His Asn Ala Lys Thr Lys Pro Arg Glu Glu Gln Tyr Asn Ser Thr
            355             360             365

Fc-Portion
Tyr Arg Val Val Ser Val Leu Thr Val Leu His Gln Asp Trp Leu Asn
            370             375             380

-continued

---Fc-Portion---
Gly Lys Glu Tyr Lys Cys Lys Val Ser Asn Lys Ala Leu Pro Ala Pro
385             390                 395                 400

---Fc-Portion---
Ile Glu Lys Thr Ile Ser Lys Ala Lys Gly Gln Pro Arg Glu Pro Gln
              405                 410                 415

---Fc-Portion---
Val Tyr Thr Leu Pro Pro Ser Arg Asp Glu Leu Thr Lys Asn Gln Val
           420                 425                 430

---Fc-Portion---
Ser Leu Thr Cys Leu Val Lys Gly Phe Tyr Pro Ser Asp Ile Ala Val
           435                 440                 445

---Fc-Portion---
Glu Trp Glu Ser Asn Gly Gln Pro Glu Asn Asn Tyr Lys Thr Thr Pro
       450                 455                 460

---Fc-Portion---
Pro Val Leu Asp Ser Asp Gly Ser Phe Phe Leu Tyr Ser Lys Leu Thr
465                 470                 475                 480

---Fc-Portion---
Val Asp Lys Ser Arg Trp Gln Gln Gly Asn Val Phe Ser Cys Ser Val
           485                 490                 495

---Fc-Portion---
Met His Glu Ala Leu His Asn His Tyr Thr Gln Lys Ser Leu Ser Leu
       500                 505                 510

The following examples describe the invention in more detail without limiting it.

EXAMPLE 1

Construction and Expression of Fc-GPVI Fusion Protein (Seq. I)

To construct the fusion protein, the vector pdC-Fc-X (described in K-M Lo et al, Protein Engineering 11: 495-500, 1998) was used. This vector encodes for a human Fc of IgG1 with a signal peptide of a murine antibody. Transcription is utilized by the enhancer/promoter of the human cytomegalovirus and the SV40 polyadenylation signal. For construction, first the extracellular part of GPVI without the leader sequence (aa 21 to aa 269) was subcloned into a Topo vector using standard PCR methods. In this step a Xma I side was introduced at the 5' part of the gene and a Hind III side at the 3' part of the gene. In addition a linker of the 3 amino acids Ser-Pro-Gly was introduced located between the end of the Fc portion and the start of the coding region of GP VI in the Fc-GP VI fusion protein. In a final step the Xma I-Hind III fragment coding for the modified extracellulare part of GP VI was cloned in frame behind the Fc fragment of IgG1 into the pdCs-Fc-X vector cut with Xma I and Hind III.

The final vector containing a dihydrofolate reductase gene as a selection marker was introduced into cells alone or together with an additional vector containing a second selection marker as neomycin. Transfection into BHK 21 cells (ATCC CCL-10, cultivated in DMEM® medium (GIBCO/BRL) supplemented with 10% fetal calf serum (FCS) and 20 mM glutamine was carried out using calcium phosphate transfections according to Graham, F. L. and van der Ebb, A. J. (Virology 52: 456, 1973) with 10-20 µg of uncut plasmid for $10^7$ cells. Stable transfectants were selected in medium containing 1 mg/ml G418 (GIBCO/BRL) and 50-200 nM methotrexate as a final concentration where only cells expressing the neomycin gene and dhfr gene can grow. After 2-3 week growth cells were cloned (0.5 cells/well) and supernatant of clones tested for production of fusion protein by Western analysis. The best producer were used for protein production.

EXAMPLE 2

Construction and Expression of GPVI-Fc Fusion Protein (Seq. II)

For construction, a standard expression vector, pcDNA3.1+ (Invitrogen) was used. In a first step a leader sequence of oncostatin M (DNA Seq.Acc. M27286) with Nhe I restriction sides introduced by PCR on both sides was cloned into the Nhe I side of pcDNA3.1. Next the hinge, CH1, CH2 and CH3 portions of Ig Gammal from a cDNA (DNA Seq.Acc. X81695 and Z17370) with a Not I side at the 5' end and a Xho I side at the 3' end of the coding region was introduced by PCR into the Not I/Xho I side of the pcDNA3.1 vector containing the leader sequence. The Ig hinge cysteines were mutated to serine residues. In parallel the extracellular part of GPVI without the leader sequence (aa 21 to aa 269) was subcloned into a Topo vector using standard PCR methods. In this step a Hind III side at the 5' part of the coding region was introduced as well as a Xho I side at the 3' part of the gene. In addition a linker of 7 amino acids (Leu-Ala-Phe-Lys-Leu-Lys-Leu) was introduced between the leader sequence and the start of the coding region of GPVI as well as an additional linker of the 3 amino acids Cys-Gly-Arg located between the end of the coding region of GPVI and the start of the Fc portion in the GPVI-Fc fusion protein. In a final step the Hind III-Not I fragment with the modified extracellular part of GP VI was cloned into the Hind III-Not I side of the pcDNA3.1 vector containing the oncostatin M leader and the coding parts of the Fc of IgG1.

The final vector containing a neomycin gene as a selection marker was introduced into cells alone or together with an additional vector containing a second selection marker as dihydrofolat reductase. Transfection into BHK 21 cells (ATCC CCL-10, cultivated in DMEM® medium (GIBCO/BRL) supplemented with 10% fetal calf serum (FCS) and 20 mM glutamine was carried out using calcium phosphate transfections according to Graham, F. L. and van der Ebb, A. J. (Virology 52: 456, 1973) with 10-20 µg of uncut plasmid for $10^7$ cells. Stable transfectants were selected in medium containing 1 mg/ml G418 (GIBCO/BRL) and 50-200 nM methotrexate as a final concentration where only cells expressing the neomycin gene and dhfr gene can grow. After 2-3 week growth cells were cloned (0.5 cells/well) and supernatant of clones tested for production of fusion protein by Western analysis. The best producer were used for protein production.

EXAMPLE 3

Production and Purification of Fc-GPVI

For production of Fc-GPVI fusion protein a stable cell clone was cultivated in an Integra Minifermenter using serumfree media in the cell compartment. The cell free supernatant was used for purification of the fusion protein. The supernatant was adjusted to pH 7.4 and the fusion protein purified using a protein A affinity column (Pharmacia®) with 0.1 mM citrat acid, pH 2.8. The protein containing fractions were neutralized using a Tris buffer with pH 9.0. In a final step using a Sephadex® G25 column a buffer change to PBS, pH 7.4 was performed. The purified protein from the supernatant was analyzed using western analysis, Biocore and ELISA. The protein was stored at −70° C.

EXAMPLE 4

Western Analysis of Fc-GPVI

Probes were loaded into slots of a 10% Tris glycin Acrylamidgel after boiling for 5 min in sample buffer containing SDS and Mercaptoethanol. After electrophoresis, proteins were transferred on PVDF membranes (BioRad®) using a Fast Blot machine (Biometra®). After blotting, the PVDF membrane was incubated in blocking buffer with blocking reagent (Boehringer Mannheim, No.: 1096176). For detection of the GPVI part of the fusion protein, the membrane was incubated with Rabbit anti-GPVI polyclonal antiserum for 2 h at room temperature. The membrane was washed with a buffer containing 0.1% Tween® 20 and blocking reagent and incubated for 1 h at room temperature with a peroxidase labeled anti rabbit antibody (Sigma®).

For detection of the Fc portion of the fusion protein, the mebrane was incubated with a peroxidase labeled goat anti human IgG, Fc fragment specific antiserum (Jackson Immuno Laboratories, Inc.) for 1 h at room temperature.

The membrane was washed and incubated with the BM chemiluminescence Blotting Substrat (Boehringer Mannheim) for 1 min. The membrane was placed into an Hypercassette with a Hyperfilm ECL (Amersham) on top. The film was developed after about 1 min exposure.

EXAMPLE 5

In Vitro Binding of Fc-GPVI at Collagen

The specific binding of GPVI-Fc at collagen is demonstrated by a calorimetric enzyme linked immunosorbent assay (ELISA). In principle, collagen coated microtiter plates are used as a matrix and GPVI-Fc as the ligand. The detection of bound GPVI-Fc is carried out by an anti-Fc antibody conjugated with horse radish peroxidase which binds specifically at the Fc moiety. After addition of peroxidase substrate, the amount of bound GPVI-Fc is reflected by an increase in absorption.

The Coating of Microtiter Plates with Collagen

The polystyrol microtiterplates are coated with 50 µl of 20 µg/ml collagen type III suspended in TRIS buffered saline pH 8.0 for 12 h. Non-bound collagen is removed by washing. Afterwards, free protein binding sites are blocked by 5% (w/v) milk powder and 0.05% (v/v) Tween® 20 both solved in HEPES buffer (pH 7.4).

The Binding Assay

Figure 4:
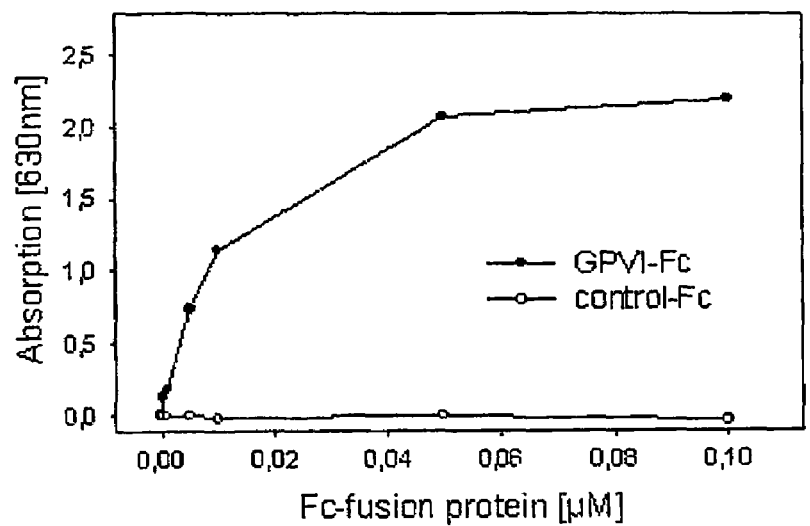

GPVI-Fc, in a concentration range of 0.1-100 nM, is solved in binding buffer (HEPES, 1% (w/v) bovine serum albumin, 0.05% (v/v) Tween® 20, pH 7.4). To evaluate the non-specific binding, a collagen non-specific Fc fusion protein is used instead of GPVI-Fc (FIG. 4).

Fifty µl of GPVI-Fc solution are given into each well. The binding of GPVI-Fc is allowed to take place for 2 h. Afterwards, fixation of collagen-bound GPVI-Fc is carried out by addition of 50 µl 20 mM glutardialdehyde applied for 10 min. After washing, an anti-Fc antibody, conjugated with horse raddish peroxidase, is added for 2 h. Finally, the amount of bound GPVI-Fc is calorimetrically detected by the peroxidase reaction.

The Detection of GPVI-receptor Antagonists

Twentyfive µl of 10 nM GPVI-Fc and 25 µl drug solution both dissolved in binding buffer are given into each well. The development of microtiter plates are carried out as described above. An antagonist of GPVI-Fc/collagen binding can easily be monitored by a reduction in absorption whereas an agonist enhance the part of bound GPVI-Fc reflected by an increase in absorption. The ELISA allows the calculation of standard parameters like the Michaelis-Menten constant (Km) for GPVI-Fc binding and the determination of the inhibition constant (Ki) for antagonists.

The Evidence for Specific GPVI-Fc Binding

The specificity of GPVI-Fc binding at collagen is indicated by:

(i) The saturation curve of GPVI-Fc binding at collagen demonstrates that collagen-binding sites are completely occupied by GPVI-Fc at a concentration above 100 nM (FIG. 4).

(ii) Neither a collagen non-specific Fc fusion protein, that is used instead of GPVI-Fc as a control, nor the horse radish peroxidase-conjugated antibody bind at collagen (FIG. 4).

Figure 5:
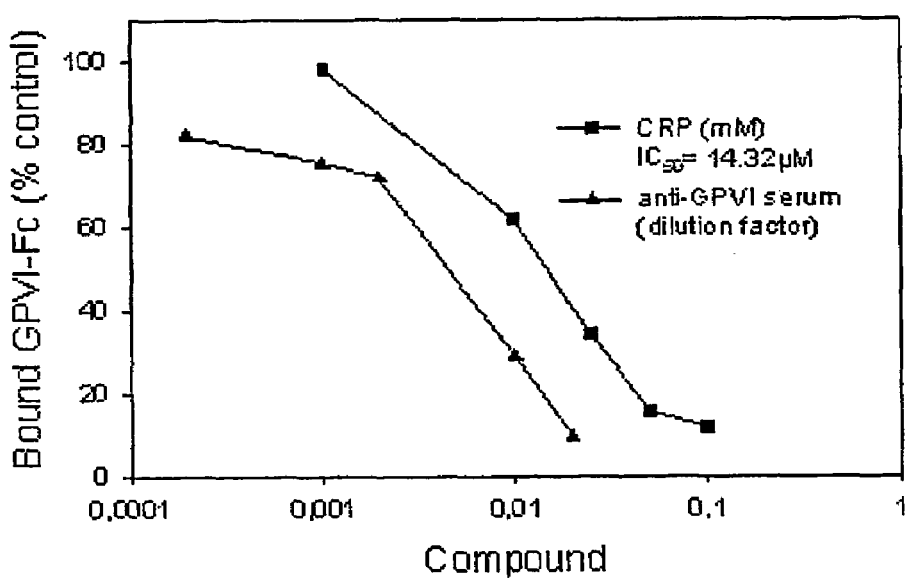

(iii) The Inhibition of GPVI-Fc binding by collagen related peptides (CRP) that are well known to bind specifically at GPVI receptors (Knight, et al., Cardiovasc. Res. 41, 450-457, 1999). The CRP amino acid sequence mimics the collagenbinding domain that interacts with the platelet GPVI receptor. In the current assay, CRP competes with collagen for GPVI-Fc that in turn leads to a reduction in collagen-bound GPVI-Fc (FIG. 5).

(iv) The inhibition of GPVI-Fc binding by a polyclonal anti-GPVI serum obtained from rabbits immunized with GPVI receptor protein that was purified from human platelets. The antiserum reduces concentration-dependently the binding of GPVI-Fc at collagen (FIG. 5).

The Therapeutic Relevance of GPVI Antagonism

Figure 6:
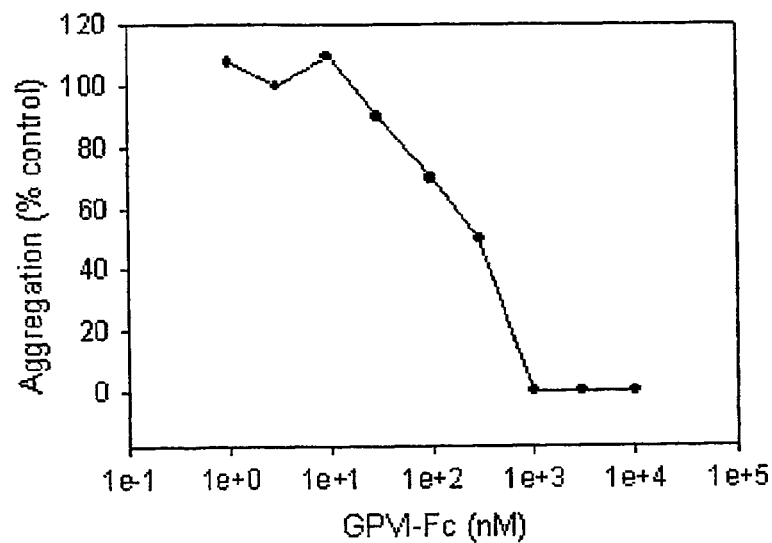

The therapeutic relevance for GPVI-antagonists to prevent collagen-induced thromboembolic complications is shown by a GPVI-Fc titration curve (FIG. 6). Briefly, stimulation of human platelets with collagen induces an aggregation within minutes. An addition of GPVI-Fc prior to collagen results in a concentration-dependent reduction of platelet-aggregation. These results indicate that GPVI-Fc compete with the platelet GPVI receptor for collagen. Therefore, collagen trapped by GPVI-Fc is no longer able to induce an aggregation of platelets. Considering the therapeutic relevance of GPVI receptor antagonism the following conclusion can be drawn from the results presented above:

(i) GPVI-Fc itself can be used as a drug to prevent collagen-induced thromboembolic complications.

(ii) Antagonism of the platelet GPVI receptor by low molecular drugs should prevent the collagen-induced aggregation.

EXAMPLE 6

Binding of GPVI to Collagen Type III (Human) Measured by Surface Plasmon Resonance (SPR)

The known interaction of GPVI to Collagen was used to develop a binding test with the BIAcore 3000. The binding of proteins to immobilized ligands can be monitored using the phenomenon of surface plasmon resonance (SPR). This technique can give results regarding the affinity and kinetics of interacting molecules in solution.

In this assay human collagen type III was immobilized on the sensor surface as stated in the methods and purified soluble GPVI was passed over the collagen surface.

Protein interactions were identified and characterized by SPR technology using the the BIAcore® 3000 instrument (BIAcore®, Freiburg, Germany) and methodology (Johnsson and Lindqvist, 1992; Johnsson et al., 1991). Coupling reagents were used according to protocols developed by the supplier. Coupling to the CM 5 sensor chip was done via activated carboxylate groups to free amine groups of human collagen type III (Sigma®). The pH-scouting and the coupling chemistry was performed under standard conditions (Johnsson and Lindqvist, 1992; Johnsson et al., 1991). For coupling the collagen was diluted to 0.125 µg/ml into 10 mM acetate buffer pH 4.5, resulting in 331 RU immobilized material.

For the binding experiments purified recombinant glycoprotein VI was used. The protein was diluted into 20 mM Hepes, pH 7.4, 150 mM NaCl, 5 mM EDTA, 0.005% Tween® 20. All binding experiments were performed at 25° C. and performed in duplicates.

The titration with glycoprotein VI was performed at concentrations ranging from 0.2 µg/ml to 50 µg/ml.

Figure 7:
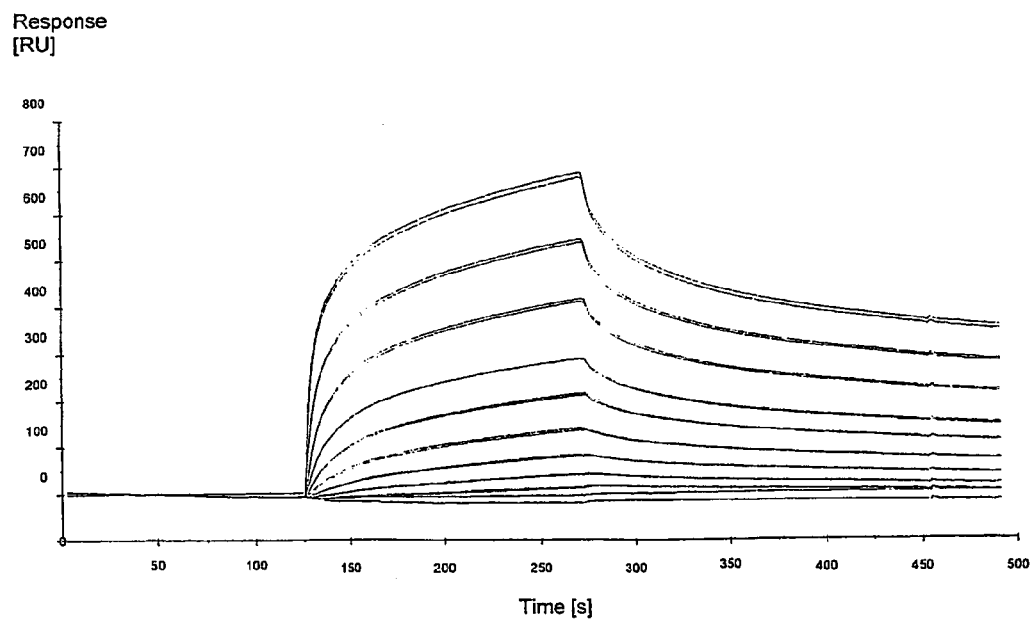

Total protein concentrations were determined by the BCA method (Pierce) The kinetic of the interaction of GPVI with collagen can be observed in the sensorgram seen in FIG. 7. In the experiment increasing concentrations of purified GPVI were passed over the collagen type III surface.

The velocity of the association for GPVI with the surface bound collagen increases with the concentration of GPVI passed over the sensor.

The binding reach saturation after about 200 seconds. The dissociation rate constant for GPVI from the collagen surface is calculated to be $0.003\ s^{-1}$, corresponding to an half life time for the complex of 230 s.

Figure 8:
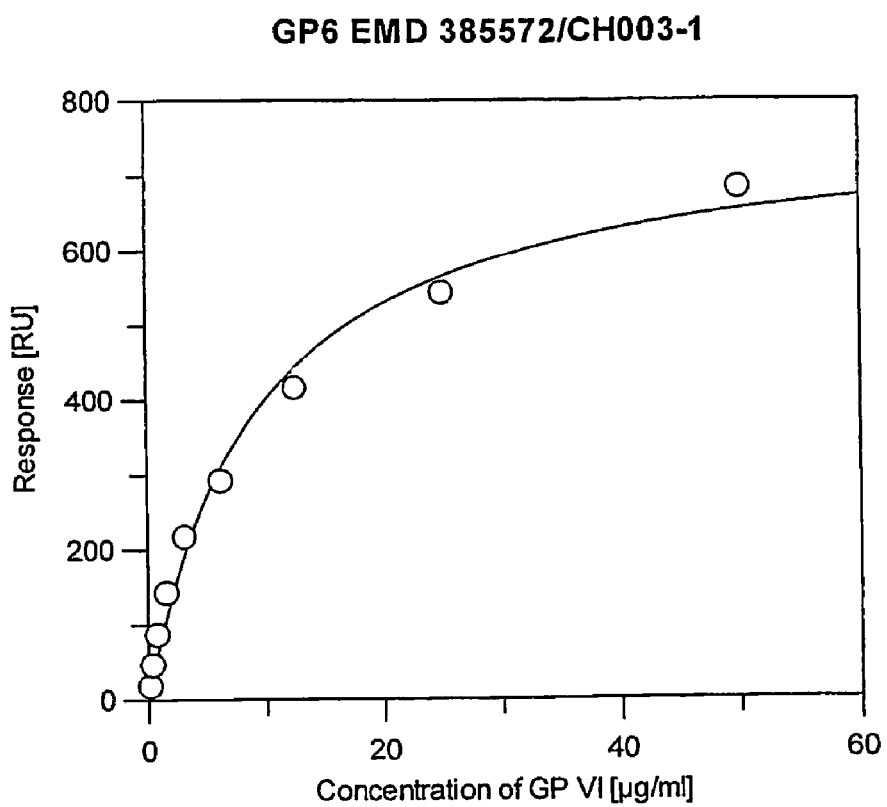

With the binding signal in the equilibrium of the binding reaction it is possible to derive the affinity or in that case the half maximal concentration of saturation for the GPVI/collagen interaction. In FIG. 8 the obtained data were plotted in the form of binding signal when the binding signal has reached equilibrium versus concentration of GPVI. By a non linear fit to a hyperbolic function with the assumption of a 1:1 binding model, a half maximal concentration of 9 µg/ml can be determined.

Assuming a molecular weight of 75000 Da and a fully active protein the equilibrium constant can be roughly estimated to $1.2 \times 10^{-7}$ M.

We claim:

1. A fusion protein comprising the amino acid sequence of SEQ ID NO: 1 or SEQ ID NO: 2.

2. A fusion protein comprising amino acids 22-501 of SEQ ID NO: 1 or amino acids 26-512 of SEQ ID NO: 2.

3. A method for producing a fusion protein according to claim 1, comprising:

a) constructing a polynucleotide which encodes the fusion protein of claim 1,
b) placing said polynucleotide in an appropriate expression vector,
c) expressing said fusion protein in a eukaryotic cell, and
d) purifying said fusion protein.

4. A medicament comprising a fusion protein according to claim 1, and saratin.

5. A medicament comprising a fusion protein according to claim 1, and streptokinase.

6. A kit comprising
a collagen coated surface,
a fusion protein according to claim 1,
an antibody which comprises a recognition site for said fusion protein and a detectable label which is an enzyme, a colored dye, a fluorescent material, a chemiluminescent material, a bioluminescent material, or a radioactive isotope.

7. A fusion protein of claim 1 which consists of the amino acid sequence of SEQ ID NO:1.

8. A fusion protein according to claim 2, which consists of amino acids 22-501 of SEQ ID NO:1 and a tag, wherein said tag is an immunoglobulin (Ig) molecule, GST, HA, FLAG, or STREP.

9. A fusion protein according to claim 2, which consists of amino acids 26-512 of SEQ ID NO:2 and a tag, wherein said tag is an immunoglobulin (Ig) molecule, GST, HA, FLAG, or STREP.

10. A fusion protein according to claim 1, which consists of the amino acid sequence of SEQ ID NO:2.

11. A fusion protein according to claim 2 which comprises a tag which is an Fc portion of an immunoglobulin (Ig) molecule.

12. A pharmaceutical pack which comprises a fusion protein according to claim 1 and a pharmaceutically acceptable carrier.

13. A pharmaceutical pack which comprises a fusion protein according to claim 2 and a pharmaceutically acceptable carrier.

14. A medicament comprising a fusion protein according to claim 2 and saratin.

15. A medicament comprising a fusion protein according to claim 2 and streptokinase.

16. A kit comprising
a collagen coated surface,
a fusion protein according to claim 2,
an antibody which comprises a recognition site for said fusion protein and a detectable label which is an enzyme, a colored dye, a fluorescent material, a chemiluminescent material, a bioluminescent material, or a radioactive isotope.

17. A method for producing a fusion protein according to claim 2, comprising:
a) constructing a polynucleotide which encodes the fusion protein of claim 2,
b) placing said polynucleotide in an appropriate expression vector,
c) expressing said fusion protein in a eukaryotic cell, and
d) purifying said fusion protein.

* * * * *